United States Patent [19]
Higgins

[11] Patent Number: 4,981,355
[45] Date of Patent: Jan. 1, 1991

[54] CALIBRATION CUP FOR IN VITRO CALIBRATION OF AN OXYGEN SATURATION MONITOR AND METHOD OF USING SAME

[75] Inventor: Michael J. Higgins, Mission Viejo, Calif.

[73] Assignee: Baxter International Inc., Deerfield, Ill.

[21] Appl. No.: 351,678

[22] Filed: May 12, 1989

[51] Int. Cl.⁵ .............................................. G02B 23/24
[52] U.S. Cl. .................................... 356/243; 128/634; 356/41
[58] Field of Search .................... 356/41, 243; 128/634

[56] References Cited

U.S. PATENT DOCUMENTS

| | | | |
|---|---|---|---|
| 4,050,450 | 9/1977 | Polanyi et al. | 356/243 X |
| 4,650,327 | 3/1987 | Ogi | 356/243 |
| 4,744,656 | 5/1988 | Moran et al. | 356/243 |
| 4,796,633 | 1/1989 | Zwirkoski | 356/243 X |
| 4,823,167 | 4/1989 | Mouska et al. | 356/243 |

Primary Examiner—Davis L. Willis
Assistant Examiner—Matthew W. Koren
Attorney, Agent, or Firm—Debra D. Condino

[57] ABSTRACT

A calibration device is provided for in vitro calibration of a light guide. The calibration device has a surface defining a cavity having an open end and a closed end opposite the open end. The opening is sized to receive the end portion of a light guide and a stop is provided near the closed end to prevent the light guide from contacting the inner surface of the closed end and to define an air gap between the end face of the light guide and the inner surface of the closed end. The inner surface of the closed end is flat and perpendicular to the longitudinal axis of the light guide. The light guide directs light from the end face of the light guide across the gap and against the flat surface. The calibration device is formed of a suitable material, such as polyethylene, with a plurality of light scattering particles and a plurality of light absorbing particles having neutral density filter properties uniformly distributed therein. Preferred light absorbing particles that have the properties of a neutral density filler are carbon black.

5 Claims, 3 Drawing Sheets

CALIBRATION CUP FOR IN VITRO CALIBRATION OF AN OXYGEN SATURATION MONITOR AND METHOD OF USING SAME

FIELD OF THE INVENTION

This invention relates generally to optical catheter calibration, and more particularly to a catheter calibration device for in vitro calibration of an optical catheter and an oxygen saturation monitor.

BACKGROUND OF THE INVENTION

In vitro calibration of an optical catheter, which may or may not include calibration of the associated instrumentation, is often accomplished with a calibration element of known optical properties placed over the distal end of the catheter tube. Light propagated through transmitting optical fibers in the catheter tube returns from the calibration element through receiving optical fibers in the catheter to suitable instrumentation for measuring and processing the optical signal. The measurements taken provide an optical characterization of the catheter and instrumentation which is used to quantify subsequent measurements taken of a sample under examination.

In calibrating the catheter, it is important that the end portion of the catheter tube be retained in a preferred proximity with the calibration element, and that this be done in a sterile environment while enabling a convenient, repeatable calibration prior to catheter use. Existing devices intended to accomplish this have certain drawbacks which need to be overcome.

For example, U.S. Pat. No. 4,322,164 to Shaw, et al., describes a box that is sealed with the catheter in a dual-envelope sterilizable package so that the end portion of the catheter is located in the box. In order to calibrate the catheter, the box is actuated by pressing a trigger mechanism through the package wrapper, and this causes a resilient holder to grip the catheter tube as a spring drives the calibration element against the catheter tip. Thus, the end portion of the catheter is placed and retained against the calibration element for calibration purposes, but only with a relatively complicated and expensive mechanical device.

U.S. Pat. No. 4,650,327 to Ogi discloses a calibrating device including a tube having a reference block therein which is spring loaded into compliant engagement with the distal end of the optical catheter. A releasable strap tightly secures the catheter to the calibration device. The packaged catheter can then be calibrated by removing the proximal end from the sealed package and connecting it to a processor for performing the calibration operation. Again, the catheter is retained against the calibration element with a relatively complicated and expensive mechanical device.

The reference block in Ogi and Shaw is described as a solid cylindrical element formed of a silicone resin, having a plurality of tiny particles scattered throughout its mass to provide scattering and reflecting surfaces for the light beams transmitted by the catheter. Ogi states that the particles should have dimensions within the range of from about 0.02 to about 2.0 microns.

Ogi states that the mass should be translucent and compliant at the surface so that it will yield when pressed against the rigid surface of the catheter, thereby insuring a snug fit. Shaw states that the solid mass should be substantially transparent, compliant at the surface and noncompressible. Shaw states that for measuring oxygen saturation of the blood, the particles may be titanium dioxide but that other light-scattering particles such as oxides, sulfates and carbonates of magnesium, barium and calcium or the like may also be used. See Column 3, line 67 to Column 4, line 41 of Shaw and Column 3, line 51 to Column 4, line 9 of Ogi.

U.S. Pat. No. 4,050,450 to Polanyi et al., discloses a calibration device described as a generally tubular reflecting member aligned with and adjacent to the distal end of the catheter. The reflecting member may be vinyl tubing or the like which may be removably or fixably positioned about the distal end of the catheter to reflect light directed thereon from the catheter when in air or a clear sterile solution for calibration. Polanyi states that while a variety of tubing materials and coloration are satisfactory a white-pigmented, flexible vinyl tubing is preferred. However, since the calibration element or tube is optically open at its distal end, the device is not immune to ambient light.

U.S. Pat. No. 4,744,656 to Moran et al., discloses a calibration device, referred to as a boot, into which the catheter tip is placed and held gently by a detent formed within the cavity of the boot. A calibration substance faces the tip in a mechanically and optically standardized calibration relationship to reflect light from within the catheter back into the catheter. The calibration substance is held in constant, precise contact with the tip by close fit between the tip and the precision-molded internal surfaces of the cavity. The calibration substance is preferably a homogeneous suspension of reflecting particles in a translucent or transparent polymer. The boot is preferably injection molded from the calibration substance, except for a rigid opaque outer skin. The specification describes the base material as a substantially transparent, medical-grade moldable high-strength silicone. The filler is described as silica-free magnesium oxide, obtained as a white powder with a maximum particle size of roughly 1/30th of a micron. See Column 10, line 58–64.

The subject matter of the present application relates to the subject matter of commonly assigned U.S. Pat. No. 4,796,633 to Zwirkoski, entitled Method and Apparatus for In Vitro Calibration of Oxygen Saturation Monitor, and commonly assigned U.S. patent application, Ser. No. 942,356, entitled Catheter Calibration Device, in the name of Manska, et al. The disclosures of the Zwirkoski patent and the Manska patent application are incorporated herein by reference in their entirety.

Specifically, Zwirkoski discloses a calibration element comprising an elongated tubular wall open at one end with an integral end wall closing the other end. The end wall defines a curved cavity opening toward the open end of the tubular wall. The calibration element is adapted to receive a light guide through the tubular wall and into the cavity. The cross-section of the cavity is progressively reduced distally to limit the extent to which the light guide can be advanced into the cavity so that the end face of the light guide is spaced from the inner surface of the end wall to define a hemispherical gap. The end wall and the gap are adapted to return a known ratio of the light directed into the gap from the end face of the light guide.

The catheter calibration device disclosed in the Manska application includes the calibration element of Zwirkoski and a clamp member of resiliently deformable material with which to hold the catheter tube and retain the end portion of the tube in the cavity of the calibration element. A retainer member is also provided to retain the clamp member in generally fixed proximity to the open end of the cavity of the calibration element. A light-blocking cap encases the optically active portion of the calibration element.

The Zwirkoski calibration element has a spherical inner surface with relatively thin walls approximately 0.045 inches thick and requires the use of an opaque optical barrier (styrene backing) to obtain the correct optical ratio and to prevent ambient light from being received by the optical fiber in the catheter. Without the opaque barrier, the back scattered ratio is out of the acceptable range.

In its simplest form, the mathematical representation of the optical signals in a particulate media is the Beer-Lambert-Bauger equation: $I = I_o \times \exp(Q_{ext} \times N \times d)$ where I=transmitted light intensity, $I_o$=incident light intensity, $Q_{ext}$=extinction coefficient at a specific wavelength, N=number of particles per unit volume, and d=path length through the particulate medium.

The optically active part of the Zwirkoski calibration element is sufficiently thin to allow the optical signal $I_o$ to be transmitted through the walls of the calibration device reflect off the opaque optical barrier and be measured as part of the return signal by the receiving fiber. The wall thickness of the calibrator is variable due to manufacturing tolerances. The air gap between the calibrator and opaque optical barrier is variable. The shape of the catheter tip and the polishing depth also varies from catheter to catheter thereby varying the length of the air gap between the end face of the catheter and the inner surface of the calibrator. Finally, the opaque optical barrier is not controlled for its optical absorption and reflectance properties. Thus, the path length d in Beer's equation is variable resulting in undesirable variation in the reference signal.

Since the inner optical surface is smooth, some of the transmitted light is reflected from the surface and is returned to the receiving fiber without being acted upon by the scattering and absorbing materials in the calibration device. This is known as specular reflection. Specular reflection is only of concern when the sending and receiving fibers are parallel to each other and I is the backscattered light. Specular reflection is an undesirable signal for calibration purposes since the signal is not acted upon by the scattering and absorbing materials within the calibration device.

The amount of specular reflection received by the light guide is determined by the distance of the reflecting surface from the end face of the light guide and the shape of the reflecting surface. The spherical shape of the inner optical surface in the Zwirkoski calibrator functions to focus the specular reflection at the catheter tip, thereby aggravating the effects of specular reflection. Further, the spherical inner surface of the Zwirkoski calibrator moves the end face of the catheter away from the optical surface of the calibrator. The increased distance between the reflecting surface and the receiving fiber increases the amount of specular reflection.

SUMMARY AND OBJECTS OF INVENTION

It is an object of the present invention to provide an improved in vitro calibration device wherein the use of an opaque optical barrier is not required.

It is another object of the present invention to accommodate catheter tips of various dimensions while maintaining a fixed air gap dimension.

It is another object of the present invention to provide a neutral density filter to control the back scattered light intensities.

It is another object of the present invention to maintain accurate control of the ratio of back scattered light intensity and to substantially prevent specular reflection.

In general, the present invention provides an improved calibration element having a surface defining a cavity with an opening at one end. The opening is sized to receive the distal end portion of a light guide. To provide immunity to ambient light and to prevent the escape of light from the cavity, the cavity is essentially optically closed, except for such opening.

Means is provided for releasably positioning the end portion of the light guide in the cavity, with the end face of the light guide spaced from the surface of the cavity opposite the opening to define a gap. The surface which defines the cavity need not be compliant and is preferably rigid. The surface opposite the opening is a flat surface perpendicular to the longitudinal axis of the light guide. During calibration, a light source transmits light at least at one wavelength, preferably at two wavelengths, through the light guide, out the end face of the light guide, across the gap and against the flat surface of the cavity. The flat surface helps to prevent specular reflection.

The air gap is sufficiently large to allow a separation between the end face of the light guide and the optical surface, but sufficiently small to substantially prevent specular reflection. The minimum separation should be the same as the wavelength of the light transmitted or greater. For example, if the light source transmits light at 660 nm, the minimum separation between the end face and the optical surface should be at least 660 nm or greater. If two or more wavelengths of light are used to calibrate the device, the air gap, i.e., the separation between the end face of the light guide and the optical surface, must be the same as or greater than the longer wavelength. A preferred air gap is 0.0015 inch plus or minus 0.0005. The air gap also serves to preserve the integrity of the heparin coating on the end face of the fiber optics in the catheter tip without affecting the other optical properties of the calibration system.

The positioning means for the light guide establishes the size of the gap, and the size of the gap should be repeatable so that the attenuating effects of the gap will be repeatable. To meet these requirements in a simple, inexpensive construction, the positioning means of the present invention includes a stop formed in a portion of the surface which defines the cavity. The stop prevents forward movement of the distal face of the light guide or catheter and thereby maintains a fixed air gap despite dimensional tolerances in the shape and polishing depth of the catheter tip.

The calibration element and the gap are adapted to return a known ratio of light at the selected wavelengths. Accordingly, contact between the calibration element and the end face of the light guide is not required as in the prior art devices. The light returned is transmitted proximally along the light guide to a measuring device which measures the intensity of the light returned. This information provides an optical characterization of the light guide and the other components of the system for calibration purposes.

The calibration element can be of simple and inexpensive construction and be disposable. For example, the calibration element may take the form of a calibration cup which comprises an elongated, conically shaped or tubular shaped wall open at one end with an end wall closing the other end. The elongated wall and the end wall can be integrally molded. With this construction, the end wall defines the cavity, and the cavity opens toward the open end of the elongated wall. The cavity is adapted to receive the end portion of the light guide and the end wall provides the calibration reference for use in calibrating the catheter and the associated components and instrumentation.

The present invention seeks to solve the problems experienced with the Zwirkoski calibrator and prior art calibrators by increasing the path length of the optical signal within the calibration material. Specifically, this is accomplished by increasing the thickness of the calibrator walls so that the wall thickness is greater than the path length through the calibration material. When using a non-compliant plastic material for molding there are physical limitations for wall thickness to maintain a well-defined surface. Based on the maximum wall thickness allowed by the molding process before material shrinkage occurs, the concentration N of particles within the scattering medium is adjusted to prevent the transmitted light from escaping from the calibration device. The increased wall thickness also prevents escape of transmitted light. A preferred wall thickness is 0.135 inch and a preferred scattering particle concentration is 0.6 wt.%.

The calibration device of the present invention is preferably constructed of a plastic material, such as polyethylene. Low density polyethylenes (LDPE) are preferred. A plurality of light scattering and absorbing particles are uniformly dispersed within the optically active area of the calibration device. The scattering particles are preferably $TiO_2$, but other known scattering particles may be used, such as oxides, carbonates and sulfates of magnesium, barium and calcium or the like. The present invention uses the concentration of $TiO_2$ suspended in a LDPE base to maintain accurate control of the ratio of backscattered light intensities. The particle sizes of $TiO_2$ are critical and should be in the range of from about 0.2 to 2.0 microns. A preferred size is in the range of from about 0.2 to 0.6 microns.

The backscattered intensity of each wavelength used should be similar to that of blood so that the instrument does not exceed its dynamic range during in vitro calibration. The present invention achieves this end by adding to the calibration material light absorbing particles that absorb each wavelength used similarly. The calibration material thus functions as a neutral density filter. Preferred light absorbing particles for this purpose are carbon black powder. Carbon black powder attenuates the backscattered $I_1$ and $I_2$ intensities similarly to a specified I within the dynamic range of the measuring instrument.

The use of a neutral density filter solves many of the problems encountered with prior art devices and the Zwirkoski calibrator. A neutral density filter eliminates the need for a separate opaque optical barrier. Prior art calibrators and the Zwirkoski calibrator use an opaque cap to attenuate ambient light and eliminate external influences (including ambient light) that may affect the ratio of backscattered light intensities. Use of a neutral density filter controls the backscattered light intensities and provides immunity to ambient light. Carbon black is an advantageous neutral density filter because it is stable for long periods of time and eliminates the need for light absorbing dyes.

The present invention provides additional advantages. It provides a fixed reference for accurate photometric measurements in an oximeter system without the need for any moving parts. The user is not required to manipulate the system to perform an in vitro calibration. The calibrator of the present invention is capable of multiple EtO sterilizations without affecting the accurate control of the ratio of backscattered light intensities. It is inexpensive to make, and accommodates catheter tips of various dimensions while maintaining a fixed air gap dimension.

The invention together with additional features and advantages thereof may be best understood by reference to the following description taken in conjunction with the accompanying drawings.

DESCRIPTION OF THE PREFERRED EMBODIMENT

Figure 1:
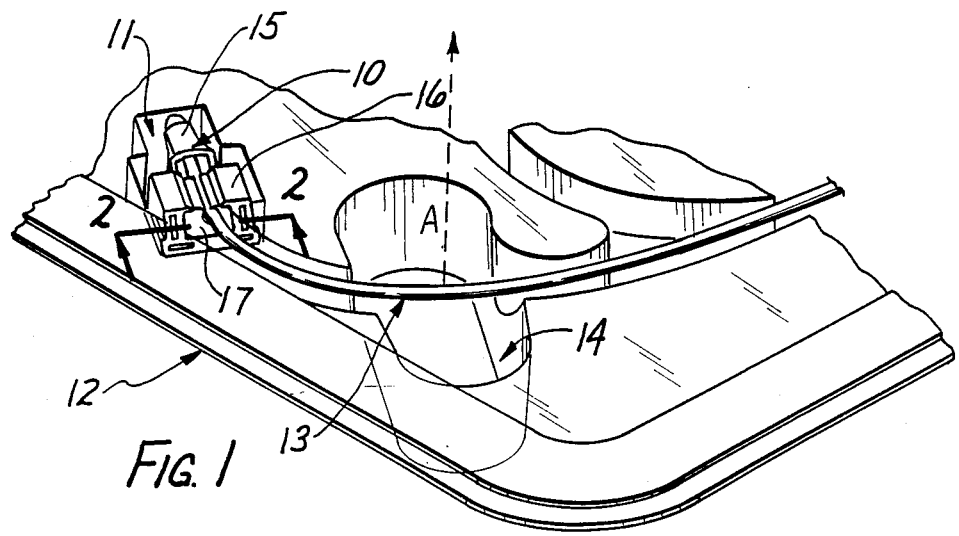
FIG. 1 is an isometric view of a portion of a packaging tray in which is disposed an optical catheter and catheter calibration device constructed according to the present invention.

Referring to FIG. 1, there is shown a catheter calibration device 10 constructed in accordance with the present invention. The device 10 is mounted in a recess 11 in sterile packaging tray 12 where it retains an optical catheter 13 pre-positioned in a desired calibration position. The tray is preferably of the type disclosed in commonly assigned, co-pending application, Ser. No. 270,320, entitled PACKAGE AND LID WITH CONTROLLED TEARING MEANS in the name of Bickelhaupt, the disclosure of which is incorporated herein by reference in its entirety. The package is designed such that one portion of the lid can be torn away to expose the optical connector while the optical catheter and calibration cup remain enclosed in the tray. The optical connector can then be connected to the optical instrument for calibrating the catheter in the package. Thus, the invasive portion of the catheter remains in a clean and protected environment during calibration.

Once calibration is completed, the second portion of the lid is torn open to expose the catheter and calibration cup. The surgeon can then grasp the catheter 13 at the finger well 14 (FIG. 1) and lift it as indicated by arrow A in a direction generally normal to the tray 12, thereby dislodging the catheter 13 from the calibration device 10 for use.

Although the calibration device 10 is shaped and dimensioned for use with tray 12, the inventive concepts are equally applicable to any of many other shapes and sizes that the elements to be described may take. Generally, the calibration device includes the following elements, a calibration element or cup 15, a retainer member 16, and a clamp member 17.

Figure 6:
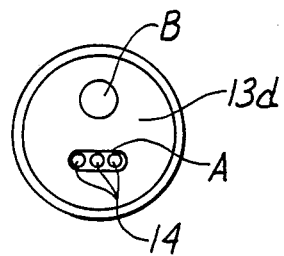
FIG. 6 is an end elevational view of a distal end of the optical catheter.

The catheter 13 (FIGS. 1, 3 and 4) is a conventional type of catheter such as an optical oximetry catheter, and includes a catheter tube 13a that extends past a balloon portion 13b to a distal end portion 13c that terminates in an end face 13d (FIG. 6). FIG. 6 shows the end face 13d with optical fibers 14 in lumen A and the distal port 16 of the through lumen B which is generally used for pressure measurements. In a broad sense, the catheter tube 13a constitutes a light guide.

During calibration, light propagated through the transmitting optical fiber in the catheter tube 13a passes out the face 13d (FIG. 6) and impinges upon the inner surface 19 of the calibration element 15. A major portion of the light penetrates the inner surface 19, and the light is scattered, reflected and absorbed by the particles in the calibration material so that a portion returns back through the receiving optical fibers in the catheter tube 13a for measurement by suitable instrumentation (not shown) connected to a proximal end of catheter 13. The intensity of the light returned at two or more wavelengths is measured by the instrument and compared with the known ideal ratios. Adjustments are then made in the instrument to calibrate the system. Subsequent measurements of light intensities returned from the sample to be measured can then be quantified based on the calibration.

To measure oxygen saturation of the blood, an optical catheter such as catheter 13 is first calibrated as described above and then inserted into the pulmonary artery using known techniques. Light from a light source (not shown) is transmitted along the transmitting light conductor or optical fiber to the end face 13d of the catheter where it impinges upon the blood. The blood scatters, reflects and absorbs some of the light from the light conductor and returns a portion of the light along the receiving light conductor or optical fiber to the measuring and processing instrument. By comparing the intensities of light returned by the blood at two or more wavelengths, the oxygen saturation of the venous blood can be determined in accordance with know techniques. For this purpose, the light source transmits light at a selected wavelength or wavelengths depending upon the algorithm being employed.

If the catheter and instrument are not calibrated, the catheter 13, light source and instrument may introduce variables into the system which would prevent an accurate determination of oxygen saturation. Accordingly, prior to use of catheter 13 and associated components and instrumentation, calibration is performed using the calibration element of the present invention.

The calibration element 15 preferably has light-scattering, absorption, and reflection properties, which, in the aggregate, (but not necessarily individually), are similar to those of a predetermined type of sample to be examined, such as blood. The optical properties of the calibration element must be known and be repeatable from element to element in production. This is necessary so that the calibration element will do its part to return the known ratio of light at the wavelength or wavelengths of interest back to the end face of the catheter or light guide. The optical properties of the calibration element should be homogeneous so that the ratio of light returned is not affected by the relative angular orientation of the calibration element and the end portion of the catheter.

The calibration element 15 is fabricated according to known techniques, such as injection molding, using a suitable plastic base material, such as polyethylene. Low density polyethylenes are preferred. A plurality of light-scattering and absorbing particles are uniformly dispersed within the base material at least in the optically active area of the calibration device.

The scattering particles should be the same size or smaller than the magnitude of the selected wavelengths of light transmitted into the material. Due to the small size of the scattering particles, the extinction coefficient Qext is wavelength dependent. The scattering particles should have a refractive index much greater than that of the suspending medium or base material. The scattering particles are preferably $TiO_2$ but other scattering particles can be used, such as oxides, sulfates, and carbonates of magnesium, barium, and calcium or the like. The present invention uses the concentration of $TiO_2$ suspended in a polyethylene base to maintain accurate control of the ratio of backscattered light intensities. The particle sizes of the $TiO_2$ are critical to maintain accurate control of the ratio and are preferably in the range of from about 0.2 to 2.0 microns. A preferred size is in the range from about 0.2 to 0.6 microns.

By changing the concentration N of the scattering particles, changes in the optical ratio $I_1/I_2$ can be made. Greater changes in $I_1/I_2$ can be made by including a dye that selectively absorbs wavelength 1 differently than wavelength 2 within the material matrix.

The backscattered intensity of each wavelength used should be similar to that of blood so that the instrument does not exceed its dynamic range during in vitro calibration. Thus, the calibration element of the present invention also includes light absorbing particles that absorb both wavelengths similarly so that the material functions as a neutral density filter. The neutral density filter attenuates the backscattered $I_1$ and $I_2$ intensities to a specified I within the dynamic range of the measuring instrument. Preferred light absorbing particles with this characteristic are carbon black powder. A preferred concentration of carbon black is 0.025 wt.%.

The neutral density filter light eliminates the need for a separate opaque optical barrier, i.e. a light blocking cap, for ambient light attenuation. Use of a neutral density filter controls the backscattered light intensities and provides immunity to ambient light. Carbon black is a very effective neutral density filter and is stable for long periods of time. The use of carbon black or other neutral density filter materials eliminates the need for dyes commonly used in previous calibration element designs.

The calibration element of the present invention is also capable of multiple Eto sterilizations without affecting the accurate control of the ratio of backscattered light intensities.

The scattering particles and neutral density filter particles may be mixed in various proportions depending upon the results desired and the thickness of the walls in the optically active portion of the calibration element. Thus, to increase light scattering, a greater percentage of light scattering particles should be used. Similarly, to increase the neutral density filter properties of the calibration element, a greater percentage of light absorbing particles with this property should be used. In the illustrated embodiment, the concentration of titanium dioxide particles is 0.6 wt. % and the concentration of carbon black is 0.025 wt.%.

The ingredients are mixed homogeneously so that the inner surface 19 and the front portion 21 of the calibration element will have homogeneous optical properties and be repeatable in production so that when a large number of the calibration elements are molded, the inner surface 19 and front portion 21 will have substantially the same reflection, absorption, and scattering properties. The preferred ingredients and proportions stated above provide light-scattering, absorption and reflection properties which, in the aggregate, mimic blood.

The surface finish of inner surface 19 is carefully controlled so that it will be the same in production from calibration element to calibration element. The surface should be smooth, free of scratches, indentations, pits and other surface defects. The desired smoothness can be obtained by using a tool machined to a mirror finish and by appropriate process control of the molding operation.

The calibration element or cup is constructed such that the end face 13d of the optical catheter may be pre-positioned in close proximity to the inner surface 19 of the catheter with a fixed air gap between the end face and the inner surface. To accomplish this end, the forward portion 21 includes an annular portion 23 (FIGS. 3 and 5) in which the end portion 13c of the catheter 13 seats.

A stop is provided at the distal end of annular portion 23 spaced proximally from the inner surface 19 so that when the catheter tip is inserted into the calibration cup, the face 13d is spaced slightly apart from inner surface 19 by a known amount to define an air gap 20. The stop therefore facilitates positioning of the face 13d without contacting the inner surface 19.

Preferably, the stop is formed by a step 39 in the surface of the cavity such that the diameter of the air gap is smaller than the diameter of the cavity proximally adjacent thereto. Thus, when the end portion 13d of the catheter is inserted into the cavity, the outer periphery of the end face 13d engages stop 39, thereby defining and maintaining a fixed air gap between the inner optical surface 19 and the end face 13d of the catheter. The stop is preferably rigid so that the catheter will not deform the stop when it is inserted into the cavity and therefore vary the air gap. The diameter of the air gap must be greater that the diameter of the lumen containing the optical fibers and the dimensions of the stop must be such that the optical path from the end face of the fibers to inner surface 19 is not blocked by the stop.

The inner optical surface 19 of the calibrator of the present invention presents a flat surface perpendicular to the axis of the optical fiber in the catheter tip as opposed to a spherical surface. The air gap is sufficiently large to allow a separation between the light guide and the optical surface but sufficiently small to prevent specular reflection from being measured. A preferred spacing is 0.0015 inch plus or minus 0.0005. The air gap also serves to preserve the integrity of the heparin coating on the in face of the gap fiber optic in the catheter tip without effecting the other optical properties of the calibration system.

The annular portion 23 of the calibration device with step 39 allows the calibration cup to accommodate catheter tips of various dimensions while maintaining the fixed air gap dimension.

In addition, the annular portion 23 defines a forward portion of the cavity having a size and shape that closely matches that of the end portion 13c of the catheter, and may even provide an interference fit for the end portion 13c. With an interference fit, the annular portion 23 also serves as aligning means for the end portion 13c, thus contributing to the retention of the end portion 13c within the cavity 25 in desired proximity with the inner surface 19.

The forward portion 21 extends to a hood portion 27 that combines with the forward portion 21 to define the cavity 25 (FIGS. 3 and 5) having a size and shape adapted to receive the end portion 13c of the catheter tube 13a. The cavity 25 extends along a cavity axis 29 (FIGS. 3 and 5) to a rearward portion 31 of the hood portion 27 that defines an open end or opening 33 of the cavity 25. The end portion 13c is inserted through the opening 33 into the cavity 25 to position it for calibration.

Figure 4:
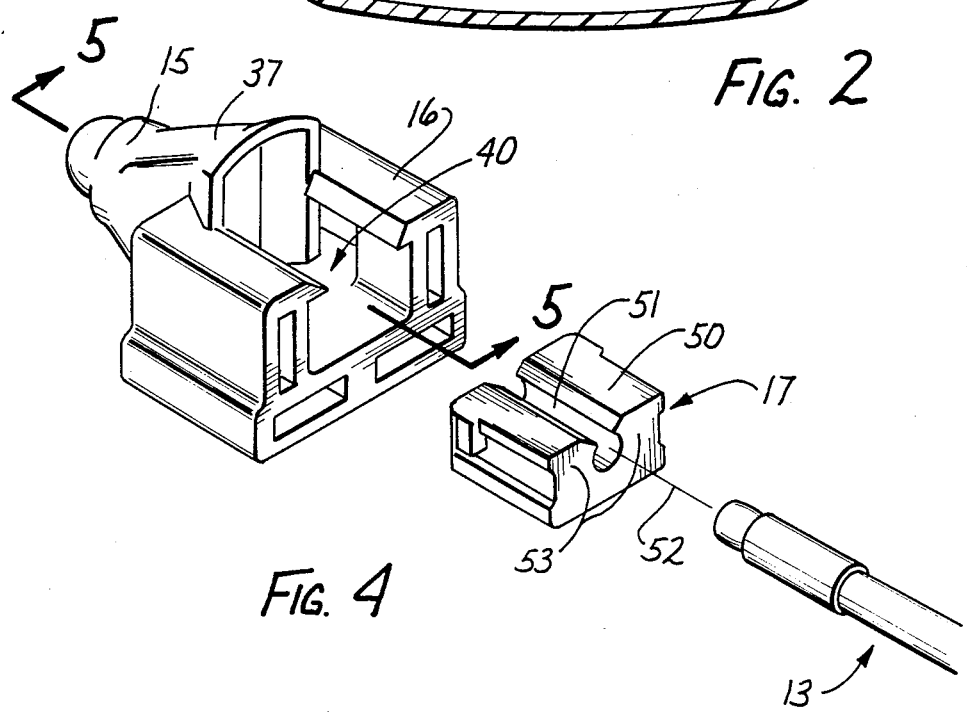
FIG. 4 is a axially exploded assembly view of the device showing axial alignment of the various components of the calibration device and the catheter tube.
Figure 5:
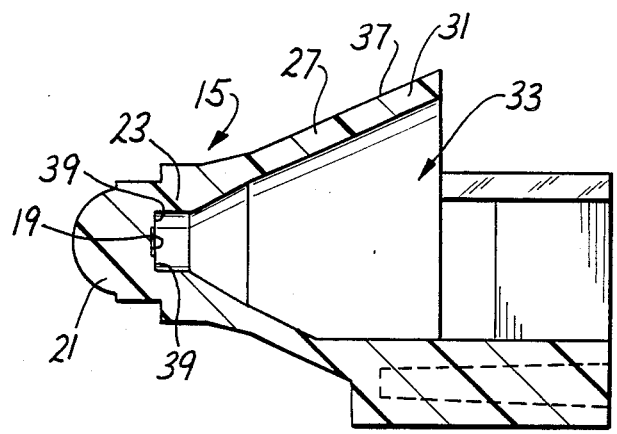
FIG. 5 is a cross-sectional view taken along line 5—5 of FIG. 4.

A conically-shaped intermediate portion 35 of the hood portion 27 is disposed toward the forward portion 21 and flares outwardly away from the cavity axis 29 toward the open end 33 to serve as shielding means to inhibit damage to the balloon portion 13b of the catheter 13. This feature is best illustrated in FIG. 5. An upwardly flared portion 37 of the hood portion 27 (FIG. 2, 4 and 5) flares upwardly away from the cavity axis toward the opening 33 at a greater rate than it does laterally, and this provides an entrance way facilitating insertion of the end portion 13c of the catheter tube 13a into the cavity 25 before placing the catheter into the clamp member 17.

Figure 3:
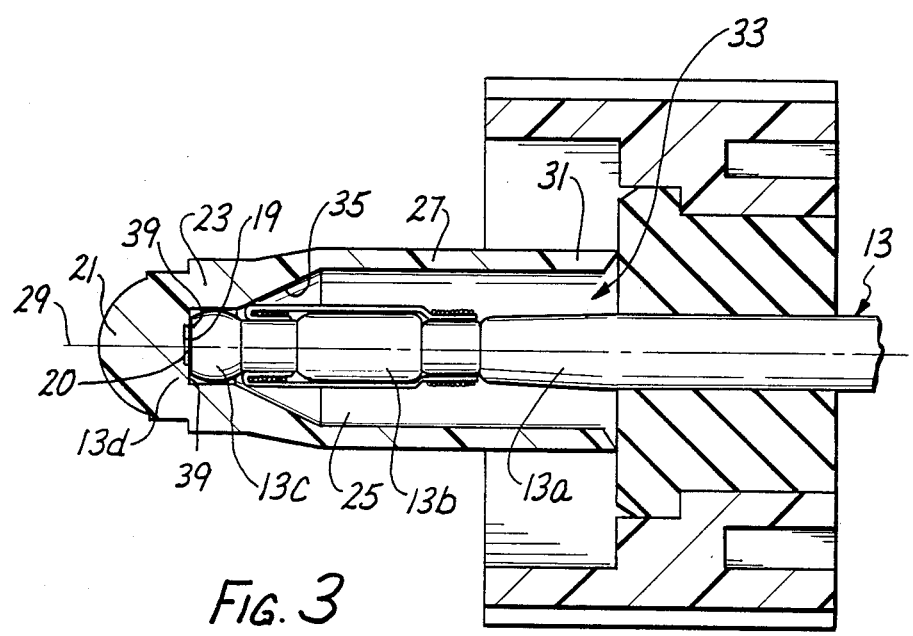
FIG. 3 is a cross-sectional view of the catheter calibration device taken along line 3—3 of FIG. 2.
Figure 2:
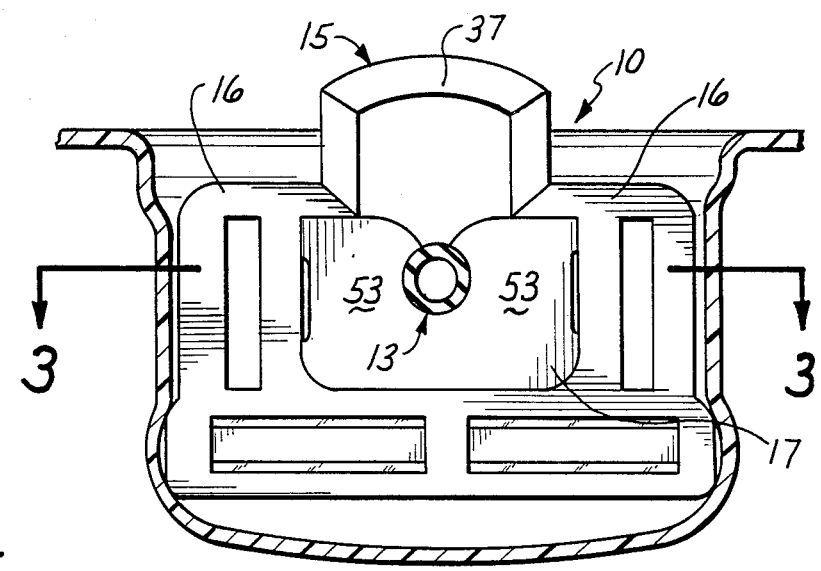
FIG. 2 is a rear end view of the catheter calibration device taken along line 2—2 of FIG. 1

The retaining member 16 and clamp member 17 which serve to retain the end portion 13c of the catheter 13 in the calibration cup are the same as that disclosed in the co-pending and commonly assigned Manska application, the disclosure of which has been previously incorporated by reference. Briefly, the retaining number 16 is preferably integrally formed with the calibration element 15 of the calibration device 10. It may however be fabricated separately and attached by suitable means such as bonding. The retaining member 16 defines a compartment 40 having a size and shape adapted to receive the clamp member 17 snugly, and serves the function of retaining the clamp member in proximity with the open end 33 of the cavity 25 as illustrated in FIGS. 2 and 3.

The clamp member 17 is composed of a suitable resiliently deformable material, such as a silicone material injected molded into the desired configuration according to known techniques. It includes an upper surface 50 and a channel-defining portion 53 that defines a longitudinally-opening slot or channel 51 extending along a channel axis 52. The channel 51 has a circularly-shaped cross-section in a plane generally perpendicular to the channel axis 52, and the channel is shaped and dimensioned so that it is slightly smaller than the cross-sectional catheter tube 13a. This result in an interference fit of the catheter tube 13a within the channel 51. Thus, the clamp member 17 deforms slightly when the catheter tube 13a is pressed into the channel 51, and it grips the catheter tube 13a resiliently to retain the catheter tube in place.

The channel-defining portion 53 serves as catheter engaging means for receiving the catheter tube by movement of the catheter tube into the channel 51 radially, i.e., along a path having a component generally perpendicular to the channel axis 52. This is done after the end portion of the catheter tube has been placed into the cavity 25. The channel-defining portion 53 also inhibits movement of the catheter 13 axially after placement into the channel 51, i.e., along the channel axis 52, which in turn inhibits movement of the end portion 13c within the cavity 25.

The silicone material of which the illustrated clamp member 17 is composed exhibits a relatively high coefficient of friction with respect to the exterior of a conventional catheter tube, and this enhances frictional engagement of the catheter tube 13a by the clamp member 17. This significantly inhibits movement of the catheter tube 13a axially, i.e., along the channel axis 52, while enabling movement radially, i.e., along a path having a component generally perpendicular to the channel axis 52. Thus, the end portion 13c of the catheter is held securely in desired proximity with the forward portion 21 of the calibration element.

Although an exemplary embodiment of the invention has been shown and described, many changes, modifications, and substitutions may be made by one having ordinary skill within the art without necessarily departing from the spirit and scope of the invention.

What is claimed is:

1. A calibration reference apparatus for use with a light guide having a longitudinal axis and an end portion that terminates in an end face, said apparatus comprising:
    (a) a calibration element having a surface defining a cavity, said cavity having an opening at one end and otherwise being essentially optically closed, said opening being sized to receive the end portion of the light guide;
    (b) means for releasably positioning the end portion of the light guide in the cavity with the end face of the light guide spaced from said surface opposite said opening to define a gap, wherein said surface opposite said opening is flat and perpendicular to the longitudinal axis of the light guide, and whereby a light guide can direct light at least at one wavelength from the end face thereof across the gap and against said flat surface opposite said opening, said positioning means including a stop proximal to said flat surface to prevent forward movement of the light guide and to maintain a fixed air gap;
    (c) said calibration element having means for returning some of the light at said wavelength which is directed against said flat surface; and
    (d) said calibration element including light absorbing particles that function as a neutral density filter.

2. An apparatus as defined in claim 1, wherein said light absorbing particles are carbon black.

3. An apparatus as defined in claim 1, wherein said stop is rigid.

4. An apparatus as defined in claim 1, wherein the means for returning light in the calibration element is a plurality of light scattering particles uniformly distributed in a matrix.

5. A method of calibrating an optical catheter having a longitudinal axis and an end portion which terminates in an end face and means for conducting light along the length of the catheter to and from the end face, said method comprising:
    (a) providing a calibration element having a surface defining a cavity, said cavity having an opening at one end and otherwise being closed, and said opening being sized to receive the end portion of the light guide, said calibration element including a plurality of light scattering particles and light absorbing particles, said light absorbing particles having the characteristics of a neutral density filter;
    (b) inserting the end portion of the catheter into the cavity to a position in which the end face of the catheter is spaced from said surface opposite said opening to define a gap and wherein said surface opposite said opening is flat and perpendicular to the longitudinal axis of the catheter;
    (c) directing light at least at one wavelength through the light-conducting means across said gap and against said flat surface;
    (d) measuring the intensity of the light returned from the calibration element through the light conducting means; and
    (e) utilizing the information obtained in said measuring step to calibrate the catheter.

* * * * *